United States Patent [19]

Shigematsu et al.

[11] Patent Number: 4,892,924

[45] Date of Patent: Jan. 9, 1990

[54] POLYCARBONATE CONTAINING COMPOUND FROM BIS(3-PHENYL-4-HYDROXYPHENYL)

[75] Inventors: Kazuyoshi Shigematsu; Takashi Nakagawa; Shuji Sakamoto, all of Sodegaura, Japan

[73] Assignee: Idemitsu Kosan Co., Ltd., Tokyo, Japan

[21] Appl. No.: 287,036

[22] Filed: Dec. 21, 1988

Related U.S. Application Data

[63] Continuation of Ser. No. 65,305, Jun. 18, 1987, abandoned.

[30] Foreign Application Priority Data

Jun. 20, 1986 [JP] Japan .................................. 61/142842
Jun. 20, 1986 [JP] Japan .................................. 61/142843
Feb. 20, 1987 [JP] Japan .................................. 62/37595

[51] Int. Cl.$^4$ ............................................. C08G 63/62
[52] U.S. Cl. .................................... 528/196; 528/171; 528/174; 528/198; 528/204
[58] Field of Search ............... 528/196, 204, 198, 171, 528/174

[56] References Cited

U.S. PATENT DOCUMENTS 3,422,065  1/1969  Wulff et al. ......................... 528/196
4,465,721  8/1984  McAlister ............................ 528/86

Primary Examiner—Harold D. Anderson
Attorney, Agent, or Firm—Antonelli, Terry & Wands

[57] ABSTRACT

A polycarbonate polymer containing repeating units represented by the following general formula

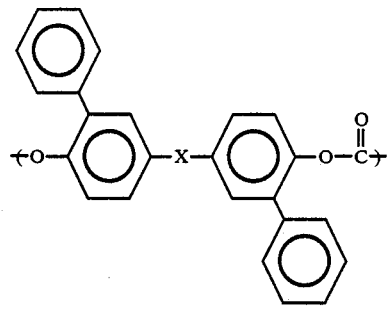

wherein: X is selected from single bond,

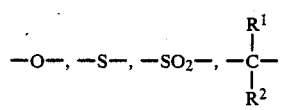

wherein: $R^1$ and $R^2$ are each independently selected from hydrogen atom; alkyl radical of 1 to 6 carbon atoms; cycloalkyl radical of 5 to 6 carbon atoms;

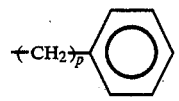

wherein p is an integer having a value of from 0 to 3; phenyl radicals substituted at para position by a substituent selected from alkoxy radicals of 1 to 5 carbon atoms, phenoxy radicals, or halogen radicals; or p-biphenylyl radical, $-(CH_2)_q-$ wherein q is an integer having a value of from 2 to 10; or

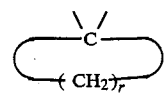

wherein r is an integer having a value of from 4 to 8, and having a reduced viscosity [$\eta sp/c$] of at least 0.2 dl/g as measured in methylene chloride at a concentration of 0.5 g/dl at 20° C.

Such polycarbonates exhibit excellent optical properties such as high birefringence, and are useful as materials for optical devices.

Also, a process for preparing the polycarbonates and novel dihydric phenols which can be used as materials for the polycarbonates are disclosed.

12 Claims, No Drawings

POLYCARBONATE CONTAINING COMPOUND FROM BIS(3-PHENYL-4-HYDROXYPHENYL)

This is a continuation of application Ser. No. 065,305, filed June 18, 1987, abandoned.

BACKGROUND OF THE INVENTION (1) Field of the Invention

The present invention relates to novel polycarbonates, to processes for the preparation of these polycarbonates, and to novel dihydric phenols that are the raw material for the preparation of the polycarbonates. Particularly, the present invention relates to novel polycarbonates that exhibit excellent optical properties such as high refractive index and are useful as, for example, materials for optical devices.

(2) Description of the Prior Art

As typical polycarbonate resins, resins obtained by reacting 2,2-bis-(4-hydroxyphenyl)propane (Bisphenol A) with phosgene or diphenyl carbonate are known. These resins are widely used as engineering plastics in many fields since they have excellent properties; i.e., high transparency, high thermal resistance, excellent mechanical properties, high dimensional accuracy in molding, etc.

In recent years, the demand for plastic optical elements has been risen since they are more advantageous over glass elements in such aspects that they are lighter in weight; they are excellent in impact strength; polishing is unessential; mass production are easier; and the mass production of nonspherical lenses is possible. While it is known that polycarbonates due to their excellent transparency and optical properties such as high refraction index are useful as materials of the plastic optical elements (c.f. Japanese Patent Application Kokai No. 126119/1983 and Japanese Patent Application Kokai No. 179224/1983), the development of novel materials having excellent optical properties has been required with the increase of the application fields of optical elements.

SUMMARY OF THE INVENTION

Under such circumstances, it is an object of the present invention to provide novel polycarbonates exhibiting improved optical properties which are useful for materials of optical devices or the like.

The inventors found, as the result of their diligent study regarding novel polycarbonates, that novel polycarbonates obtained by reacting a dihydric phenol having a particular structure with a carbonate precursor exhibit excellent optical properties such as, in particular, high refractive index, and the knowledge led them to complete the present invention.

Thus, in accordance with the present invention there are provided polycarbonate polymers consisting essentially of repeating units represented by the following general formula

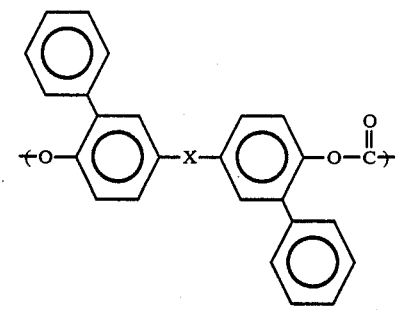

Wherein: X is selected from single bond,

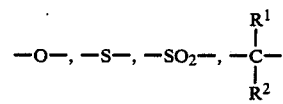

wherein: $R^1$ and $R^2$ are each independently selected from hydrogen atom; alkyl radicals of 1 to 6 carbon atoms; cycloalkyls of 5 to 6 carbon atoms;

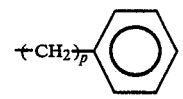

wherein p is an integer having a value of from 0 to 3; phenyl radicals substituted at para position by a substituent selected from alkoxy radicals of 1 to 5 carbon atoms, phenoxy radical, or halogen radicals; or p-biphenylyl radical, $-(CH_2)_q-$ wherein q is an integer having a value of from 2 to 10, or

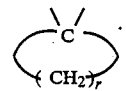

wherein r is an integer having a value of from 4 to 8, and having a reduced viscosity [η sp/c] of at last 0.2 dl/g as measured in methylene chloride at a concentration of 0.5 g/dl at 20° C.

The polycarbonate polymers can be prepared by, for example, a process comprising reacting a dihydric phenol having the general formula

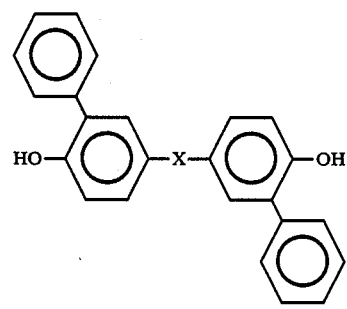

wherein x is as defined above, and a carbonate precursor.

According to the present invention there are further provided polycarbonate copolymers consisting essentially of repeating units represented by the general formula hereinabove

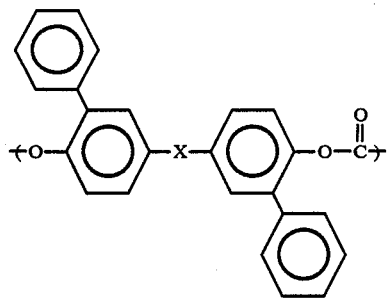

and repeating units represented by the following general formula

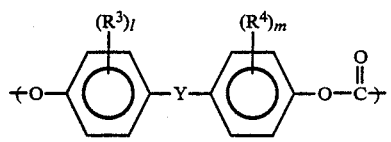

wherein: Y is selected from single bond,

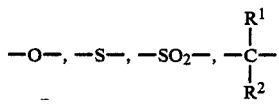

wherein: $R^1$ and $R^2$ are each independently selected from hydrogen atom; alkyl radicals of 1 to 6 carbon atoms; cycloalkyl radicals of 5 to 6 carbon atoms;

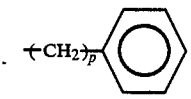

wherein p is an integer having a value of from 0 to 3; phenyl radicals substituted at para position by a substituent selected from alkoxy radicals of 1 to 5 carbon atoms, phenoxy radical, or halogen radicals; or p-biphenylyl radical, $-(CH_2)_q-$ wherein q is an integer having a value of from 2 to 10, or

wherein
r is an integer having a value of from 4 to 8,
X and Y may be the same or different from each other,
$R^3$ and $R^4$ are each independently selected from hydrogen atom, halogen radicals, or alkyl radicals of 1 to 5 carbon atoms, and
l and m are each independently an integer having a value of from 1 to 4 and having a reduced viscosity [$\eta$ sp/c] of at least 0.2 dl/g as measured in methylene chloride at a concentration of 0.5 g/dl at 20° C.

The polycarbonate copolymers can be prepared by, for example, a process comprising reacting a dihydric phenol having the general formula

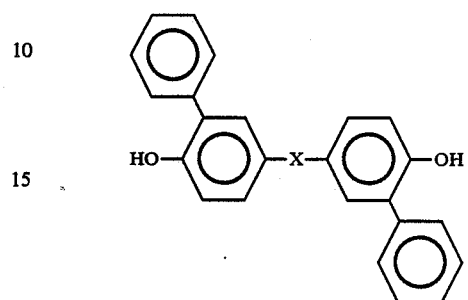

a dihydric phenol having the general formula

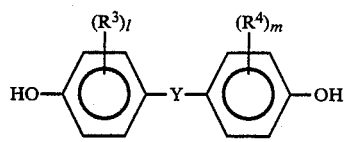

wherein X, Y, $R^3$, $R^4$, l, and m are as defined above, and a carbonate precursor.

According to the present invention there is further provided novel dihydric phenols which are a main raw material of the polycarbonates of the present invention, that is 1,1-bis(3-phenyl-4-hydroxyphenyl)methane derivatives having the following general formula

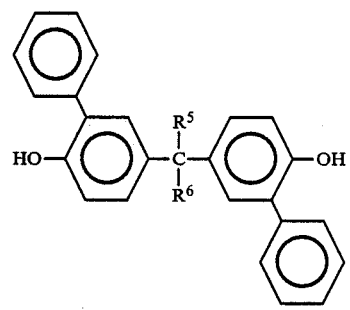

wherein:
$R^5$ is selected from hydrogen atom, alkyl radicals of 1 to 6 carbon atoms, or phenyl radical and
$R^6$ is selected from phenyl radical, phenoxyphenyl radical, alkoxyphenyl radicals of 7 to 11 carbon atoms, or p-biphenylyl radical.

DETAILED DESCRIPTION OF THE INVENTION

The dihydric phenols to be used as the raw material in the preparation of the polymer of the present invention are the compounds having the structures represented by the general formula [II] hereinabove. Some illustrative examples of the dihydric phenols include
bis(3-phenyl-4-hydroxyphenyl)methane,
1,1-bis(3-phenyl-4-hydroxyphenyl)ethane,
1,2-bis(3-phenyl-4-hydroxyphenyl)ethane, 2,2-bis(3-phenyl-4-hydroxyphenyl)propane,
1,3-bis(3-phenyl-4-hydroxyphenyl)propane,
2,2-bis(3-phenyl-4-hydroxyphenyl)butane,
1,4-bis(3-phenyl-4-hydroxyphenyl)butane,
2,2-bis(3-phenyl-4-hydroxyphenyl)octane,
1,8-bis(3-phenyl-4-hydroxyphenyl)octane,
1-phenyl-1,1-bis(3-phenyl-4-hydroxyphenyl)ethane,
diphenyl-bis(3-phenyl-4-hydroxyphenyl)methane,
1,1-bis(3-phenyl-4-hydroxyphenyl)cyclopentane,
1,1-bis(3-phenyl-4-hydroxyphenyl)cyclohexane,
3,3'-diphenyl-4,4'-dihydroxybiphenyl,
3,3'-diphenyl-4,4'-dihydroxydiphenyl ether,
3,3'-diphenyl-4,4'-dihydroxydiphenyl sulfide,
3,3'-diphenyl-4,4'-dihydroxydiphenyl sulfone,
1-(4-methoxyphenyl)-1,1-bis(3-phenyl-4-hydroxyphenyl)ethane,
1-(4-phenoxyphenyl)-1,1-bis(3-phenyl-4-hydroxyphenyl)ethane,
1-(4-ethoxyphenyl)-1,1-bis(3-phenyl-4-hydroxyphenyl)ethane,
1-(4-methoxyphenyl)-1,1-bis(3-phenyl-4-hydroxyphenyl)propane,
1-(4-phenoxyphenyl)-1,1-bis(3-phenyl-4-hydroxyphenyl)propane,
1-(4-methoxyphenyl)-1,1-bis(3-phenyl-4-hydroxyphenyl)butane,
1-(4-phenoxyphenyl)-1,1-bis(3-phenyl-4-hydroxyphenyl)butane,
1-(4-methoxyphenyl)-1,1-bis(3-phenyl-4-hydroxyphenyl)pentane,
1-(4-phenoxyphenyl)-1,1-bis(3-phenyl-4-hydroxyphenyl)hexane,
1-(4-butoxyphenyl)-1,1-bis(3-phenyl-4-hydroxyphenyl)ethane,
1-(4-methoxyphenyl)-1,1-bis(3-phenyl-4-hydroxyphenyl)methane,
1-(4-phenoxyphenyl)-1,1-bis(3-phenyl-4-hydroxyphenyl)methane,
1-(4-methoxyphenyl)-1,1-bis(3-phenyl-4-hydroxyphenyl)hexane,
1-(4-chlorophenyl)-1,1-bis(3-phenyl-4-hydroxyphenyl)ethane,
3,3-bis(3-phenyl-4-hydroxyphenyl)-1,6-diphenylhexane,
2,2-bis(3-phenyl-4-hydroxyphenyl)-1,6-bis(3-phenyl-4-hydroxyphenyl)-1,3-diphenylpropane,
1-(p-biphenylyl)-1,1-bis(3-phenyl-4-hydroxyphenyl)ethane, and the like.

Among these dihydric phenols, 1,1-bis(3-phenyl-4-hydroxyphenyl)methane derivatives having the general formula

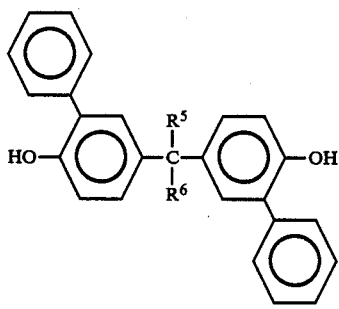

[V]

wherein $R^5$ and $R^6$ are as defined above, are novel compounds.

The 1,1-bis(3-phenyl-4-hydroxyphenyl)methane derivatives of the present invention described in the general formula [V] hereinabove can be prepared by, for example, reacting o-phenylphenol and an aldehyde or ketone having the general formula

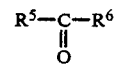

[VI]

wherein $R^5$ and $R^6$ are as defined above, in the presence of an acid catalyst, in the presence or absence of a solvent.

The typical illustrative examples of the compounds described in formula [VI] hereinabove include benzaldehyde, acetophenone, propiophenone, benzophenone, 4'-phenoxyacetophenone, 4'-methoxyacetophenone, 4'-ethoxyacetophenone, 4-formylbiphenyl, 4-acetylbiphenyl, 4-propionylbiphenyl, 4-phenylbenzophenone, and the like.

The reaction between these compounds and o-phenylphenol may be carried out either in the absence of a solvent or by using a solvent. The solvents that may be used are those being inactive in the reaction, and the preferred solvents are aromatic hydrocarbon solvents such as benzene, toluene, xylene, ethylbenzene, and the like. The catalysts to be used are acid catalysts such as hydrogen chloride, sulfuric acid, toluenesulfonic acid, trifluoroacetic acid, trifluoromethanesulfonic acid, oxalic acid, phosphorus pentachloride, polyphosphoric acid, and the like. Among these, hydrogen chloride is particularly preferable from the viewpoints of reaction accelerating property and after-treating facility. The amount of catalyst cannot be uniformly determined since it varies depending upon the kind of the catalyst employed. However, in case of employing hydrogen chloride, the amount will be usually selected among the range of from 0.5 to 10% by weight to the total amount of p-phenylphenol and the aldehyde or ketone.

In this reaction, it is desirable to use a compound containing a mercapto group as a promoter in company with the above-mentioned acid catalyst. Some illustrative examples of the compounds containing a mercapto group include alkylmercaptans such as methylmercaptan, ethylmercaptan, propylmercaptan, butylmercaptan, octylmercaptan, dodecylmercaptan, etc. aromatic mercaptans such as thiophenol, thiocresol, etc., mercapto organic acids such as mercaptoacetic acid (thioglycolic acid), mercaptopropionic acid, etc. The amount of the promoter employed is usually in the range of from 0.1 to 5% by weight to the total amount of o-phenylphenol and the aldehyde or ketone. With regard to the ratio between o-phenylphenol and the aldehyde or ketone employed, it is desirable to use o-phenylphenol in an amount larger than the stoichiometry, and 2.2 to 6 mol of o-phenylphenol is usually used per one mol of the aldehyde or ketone.

Although the reaction temperature cannot be uniformly determined since it varies depending upon the kind of the aldehyde or ketone and catalyst and the like, it is generally selected among the range of from 20° to 150° C. Although the reaction pressure is not particularly restricted and it may be any of reduced pressure, atmospheric pressure, and increased pressure, the reaction can usually be carried out advantageously under atmospheric pressure. Further, although the reaction time varies depending upon the kind of the materials, the kind and amount of the catalyst and promoter, and the like, it is usually about 5 to 200 hours.

In the process for preparing the polycarbonates of the present invention, the dihydric phenols of general formula [II] hereinabove may be used as the material either individually or in a mixture of two or more of them mixed in an optional ratio. In addition to the dihydric phenols of general formula [II] hereinabove, a mixture thereof further mixed with one or more of the dihydric phenols of general formula [IV] hereinabove may be employed as the material.

The term polycarbonate copolymers as used herein is meant to specify the polycarbonates obtained by copolymerizing the dihydric phenols of general formula [IV].

Some illustrative examples of the dihydric phenols of general formula [IV] include 2,2-bis(4-hydroxyphenyl)propane, 2,2-bis(3-methyl-4-hydroxyphenyl)propane, bis(4-hydroxyphenyl)methane, 2,2-bis(4-hydroxyphenyl)butane, 2,2-bis(4-hydroxyphenyl)octane, 4,4-bis(4-hydroxyphenyl)heptane, 2,2-(3,5,3',5'-tetrabromo-4,4'-dihydroxydiphenyl)propane, (3,3'-dichloro-4,4'-dihydroxydiphenyl)methane, bis-(3,5-dimethyl-4-hydroxyphenyl)ether, bis-(3,5-dimethyl-4-hydroxyphenyl)sulfone, bis-(3,5-dimethyl-4-hydroxyphenyl)sulfide, bis-(3,5-dimethyl-4-hydroxyphenyl)cyclohexane, and the like.

Preferred dihydric phenols [IV] to be employed are those wherein $R^3$ and $R^4$ are hydrogen atom, and 2,2-bis(4-hydroxyphenyl)propane is particularly preferably used.

The ratio between the dihydric phenols, [II] and [IV], employed is optional, and the copolymers having a high refractive index can be obtained by increasing the proportion of the dihydric phenol [II]. The refractive index can be adjusted to the values ranging from 1.58 to 1.67 by varying the proportion of the dihydric phenol [II]. The copolymers having a refractive index of at least 1.60 can be obtained by making the content of the repeating units [I] in the resulting copolymers to not less than 20 mol %.

Some illustrative examples of the carbonate precursors include phosgene and diaryl carbonates such as diphenyl carbonate, di-p-tolyl carbonate, phenyl-p-tolyl carbonate, di-p-chlorophenyl carbonate, dinaphthyl carbonate, and the like.

Any known technique in the preparation of polycarbonates from Bisphenol A, for example, the direct reaction of dihydric phenols with phosgene, the transesterification of dihydric phenols with diaryl carbonate, or the like, may be employed for the preparation of the polycarbonates of the present invention.

In the case of the above-mentioned direct reaction of dihydric phenols with phosgene, the dihydric phenols described respectively in general formulas [II] and [IV] are reacted with phosgene, usually in the presence of an acid acceptor and a solvent. Some illustrative examples of the acid acceptors which can be employed include pyridine and an alkaline metal hydroxides such as sodium hydroxide, potassium hydroxide, and the like. Some illustrative examples of the solvents which can be employed include methylene chloride, chlorobenzene, xylene, and the like.

It is preferred that a catalyst, for example, a tertiary amine such as triethylamine, a quaternary ammonium salt, etc., is used in order to accelerate the polycondensation reaction, and it is also desirable that a molecular weight regulator such as p-tert-butylphenol, phenylphenol, etc. is used in the reaction in order to adjust the degree of polymerization. A small quantity of antioxidants such as sodium sulfate, sodium hydrosulfite, etc., can be added as the needs of the case demand.

The reaction usually carried out at temperatures ranging from 0° to 150° C., preferably from 5° to 40° C. The reaction time, which is to be varied depending on the reaction temperature, is usually from 0.5 minute to 10 hours, preferably from 1 minute to 2 hours. It is preferred to keep the pH of the reaction system at not less than 10 during the reaction.

On the other hand, in the case where the technique of transesterification is employed, the dihydric phenols having the respective general formulas [II] and [IV] hereinabove and the diaryl carbonate are mixed and reacted at high temperature under reduced pressure. The reaction is usually carried out at temperatures ranging from 150° to 350° C., preferably from 200° to 300° C., the pressure of the reaction system being decreased down to 1 mmHg or below toward the final stage of the reaction in order to distill the phenols derived from the diaryl carbonate away from the reaction system. The reaction time, which is to be varied depending upon the reaction temperature, the reaction pressure employed, etc., is usually from about 1 to 4 hours. It is preferred to carry out the reaction in an atmosphere of an inert gas such as nitrogen, argon, and the like. Additives such as the above-mentioned molecular weight regulators, antioxidants, etc. can be added to the reaction system as the needs of the case demand.

The polycarbonates of the present invention which can be prepared in such ways are novel polycarbonates and have a high refractive index. The reduced density $[\eta \text{ sp}/c]$ of the novel polycarbonates as measured in methylene chloride at a concentration of 0.5 g/dl at 20° C. is not less than 0.2 dl/g. The polycarbonates having a reduced viscosity $[\eta \text{ sp}/c]$ of less than 0.2 dl/g are so low in the degree of polymerization that they can not sufficiently satisfy the object of the present invention.

The value of refractive index of the polycarbonate copolymers of the present invention can be controlled by varying the copolymerizing composition, and, therefore, the polycarbonate copolymers of the present invention is useful as elements for optical devices.

The method for molding the polycarbonates of the present invention can be optionally selected from the methods generally employed to mold known polycarbonate resins such as injection molding, compression molding, Rolinx process which is known to be a combination technique of injection molding and compression molding, micromolding technique, and the like.

In the above-mentioned molding methods, the polycarbonates of the present invention may either be molded as it is or, as the needs of the case demand, be mixed with various additives such as esters of phosphorous acid for preventing the moldings from coloration and the deterioration of transparency, plasticizers for increasing the melt index, and the like in advance of molding process.

Further, other resins may also be mixed so long as they will not damage the characteristics of the polycarbonates of the present invention.

Some illustrative examples of the esters of phosphorous acid which can be employed include tributyl phosphite, tris(2-ethylhexyl)phosphite, tridecyl phosphite, tristearyl phosphite, triphenyl phosphite, tricresyl phosphite, tris(nonylphenyl)phosphite, 2-ethylhexyl diphenyl phosphite, decyl diphenyl phosphite, phenyl di-2-ethylhexyl phosphite, phenyl didecyl phosphite, tricyclohexyl phosphite, distearyl pentaerythrityl diphosphite, diphenyl pentaerythrityl diphosphite, and the like.

Some illustrative examples of the plasticizers which can be employed include dialkyl phthalates such as di-2-ethylhexyl phthalate, di-n-butyl phthalate, diisodecyl phthalate, ditridecyl phthalate, diheptyl phthalate, dinonyl phthalate, etc., alkyl esters of dibasic acids such as di-2-ethylhexyl adipate, di-2-ethylhexyl sebacate, etc., alkyl esters of phosphoric acid such as tributyl phosphate, trioctyl phosphate, tricresyl phosphate, triphenyl phosphate, etc., esters of epoxidized fatty acids such as epoxidized octyl oleate, epoxidized butyl oleate, etc., polyesters plasticizers, esters of chlorinated fatty acids, and the like.

The novel polycarbonates of the present invention exhibit excellent optical properties such as high refractive index, and therefore they are useful as materials of various optical devices for, for example, still cameras, video cameras, telescopes, eyeglasses, contact lenses, prisms, optical fibers, video disks, audio disks, optical memory disks, and the like.

The novel polycarbonates of the present invention are also useful as engineering plastics for material of various molded articles.

EXAMPLES AND COMPARATIVE EXAMPLES

In order to more fully and clearly illustrate the present invention, the following examples are presented. It is intended that the examples be considered as illustrative rather than limiting the invention disclosed and claimed herein.

EXAMPLE 1

Preparation of 2,2-bis(3-phenyl-4-hydroxyphenyl)propane 510 g (3 mol) of o-phenylphenol and 58 g (1 mol) of acetone were mixed and the temperature was raised to 60° C. to dissolve the mixture. To the mixture was added 10 g of mercaptoacetic acid and gaseous hydrogen chloride was blown through the mixture with stirring for 36 hours. The thus-obtained reaction product was washed three times with warm water, and the organic phase was then heated to 190° C. under reduced pressure. Subsequently, the residue was dissolved in 400 milliliters of methylene chloride, and 500 milliliters of a 2N aqueous sodium hydroxide solution was added thereto and stirred. The mixture was then cooled with ice to precipitate crystals. The crystals were washed twice with 400 milliliters of methylene chloride, washed with 500 milliliters of a 2N aqueous sodium hydroxide solution, and then subsequently added to 2 liters of 1N hydrochloric acid and stirred. The crystals were then filtered, washed several times with water, and dried under reduced pressure. Thus, 154 g of crystals were obtained (yield: 40%). The compound had a melting point of from 58° to 60° C. and a purity of 99.3%. By the results of proton NMR analysis, the compound was determined to be 2,2-bis(3-phenyl-4-hydroxyphenyl)propane having the following structure.

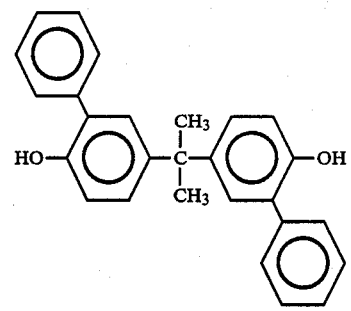

EXAMPLE 2

Preparation of 1-phenyl-1,1-bis(3-phenyl-4-hydroxyphenyl)ethane

The procedure of Example 1 was repeated with the exception that 120 g (1 mol) of acetophenone was used in place of acetone to obtain 110 g of 1-phenyl-1,1-bis(3-phenyl-4-hydroxyphenyl)ethane having the following structure (yield: 25%). The compound had a melting of from 67° to 68° C. and a purity of 99.1%.

The results of $^1$H-NMR (acetone $d_6$) were as follows.

δ (ppm): 2.17 (s, 3H), 6.89 (d, 2H), 6.96 (dd, 2H), 7.21 (m, 7H), 7.33 (t, 4H), 7.52 (d, 4H), 8.3 (b, 2H).

The molecular weight (m+) was 442.

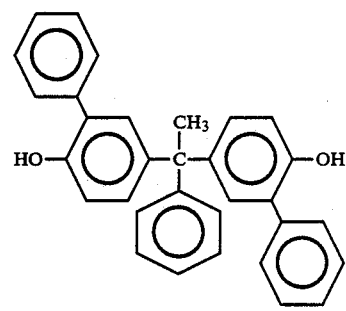

EXAMPLE 3

Preparation of 1,1-bis(3-phenyl-4-hydroxyphenyl)cyclohexane 510 g (3 mol) of o-phenylphenol and 98 g (1 mol) of cyclohexanon were mixed and the temperature was raised to 60° C. to dissolve the mixture. To the mixture was then added 150 g of 90% by weight sulfuric acid and reacted with stirring for 24 hours at 70° C. After the resulting reaction product was diluted with 1 liter of monochlorobenzene and washed three times with warm water, the organic phase was heated to 190° C. under reduced pressure to remove the solvent and the unreacted materials. After dissolving the residue in 400 milliliters of methylene chloride, 500 milliliters of a 5N aqueous sodium hydroxide solution was added and stirred. After crystals were precipitated by cooling with ice, the crystals were washed twice with 500 milliliters of methylene chloride and then washed with 300 milliliters of a 2N aqueous sodium hydroxide solution. After adding 2 liters of 2N hydrochloric acid and stirring, the crystals were filtered, washed five times with water, and then recrystallized from acetone-cyclohexane mixture solution.

Thus, 189 g of crystals were obtained (yield: 45%). The melting point of the compound was between 143° to 145° C., and the results of $^1$H-NMR (acetone $d_6$) was as follows.

δ (ppm): 1.6–1.8 (m, 10H), 6.89 (d, 2H), 7.10 (dd, 2H), 7.2–7.4 (m, 8H), 7.56 (dd, 4H).

The molecular weight (m+) of the compound was 420.

By these results, the compound was determined to have the following formula.

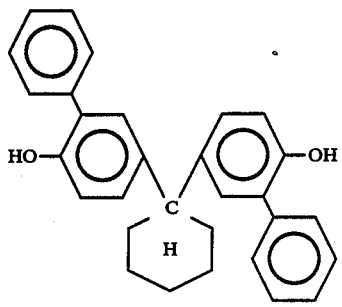

EXAMPLE 4

Preparation of bis(3-phenyl-4-hydroxyphenyl)sulfone

To a mixture of 391 g (2.3 mol) of o-phenylphenol, 100 g (1 mol) of 98% by weight sulfuric acid, and 100 g of chlorobenzene was added 9.5 g (0.05 mol) of benzenesulfonic acid and heated with stirring. While the generated water was distilled away with chlorobenzene and the organic phase of the distillate was refluxed into the reaction vessel, the reaction was carried out for 10 hours. At the time when the distilled water amounted to 36 milliliters and the temperature in the reaction vessel rose to 165° C., the reaction mixture was cooled by adding 500 milliliters of xylene to precipitate crystals. The crystals were recrystallized from acetone-cyclohexane mixture solution to obtain 340 g of a product (yield: 85%). The melting point of the product was between 251° to 252° C. and the results of $^1$H-NMR (acetone $d_6$) were as follows.

δ (ppm): 7.16 (d, 2H), 7.31–7.47 (m, 6H), 7.58 (d, 4H), 7.83 (dd, 2H), 7.21 (d, 2H).

The molecular weight (m+) of the product was 402.

By these results, the product was determined to have the following formula.

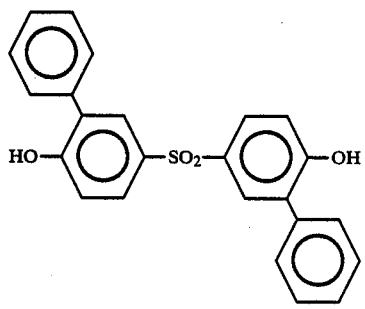

EXAMPLE 5

Preparation of 1-(4-phenoxyphenyl)-1,1-bis(3-phenyl-4-hydroxyphenyl)ethane 510 g (3 mol) of o-phenylphenol, 212 g (1 mol) of 4'-phenoxyacetophenone, and 9.2 g of mercaptoacetic acid were mixed, and the mixture was dissolved by heating to 60° C. and stirred. After adding 117 g of 98% by weight sulfuric acid, the mixture was reacted for 12 hours at 70° C. After the conclusion of the reaction, the product was cooled, diluted by adding 3 liters of methylene chloride, and then washed three times with 2 liters of water. Subsequently, 500 milliliters of a 5N aqueous sodium hydroxide solution was added and crystals were obtained by cooling with water. Then, after washing the crystals with methylene chloride, the crystals were dispersed in 3 liters of water, and hydrochloric acid was added till the pH was lowered to not more than 1. Subsequently, the crystals were filtered out, washed with water, and then recrystallized by the use of a toluene-hexane mixture solvent to obtain 235 g of 1-(4-phenoxyphenyl)-1,1-bis(3-phenyl-4-hydroxyphenyl)ethane.

Yield of the above-mentioned product was 44% (basing on 4'-phenoxyacetophenone), and the melting point thereof was between 125° to 129° C.

The results of $^1$H-NMR (acetone $d_6$) analysis were as follows.

δ (ppm): 2.10 (s, 3H), 6.82 (s, 4H), 6.9–7.4 (m, 17H), 7.54 (d, 4H).

The molecular weight (m+) determined by mass spectrum analysis was 534.

EXAMPLE 6

Preparation of 1-(4-methoxyphenyl)-1,1-bis(3-phenyl-4-hydroxyphenyl)ethane

The procedure of Example 5 was repeated with the exception that 15 g (1 mol) of 4'-methoxyacetophenone was used in place of 4'-phenoxyacetophenone. Resultantly, 160 g of 1-(4-methoxyphenyl)-1,1-bis(3-phenyl-4-hydroxyphenyl)ethane was obtained. The yield was 34% (basing on 4'-methoxyacetophenone), and the melting point was between 142° to 145° C.

The results of $^1$H-NMR (acetone $d_6$) were as follows.

δ (ppm): 2.21 (s, 3H), 3.54 (s, 3H), 6.82 (d, 2H), 6.92 (d, 2H), 6.98 (dd, 2H), 7.04–7.22 (m, 6H), 7.25–7.40 (m, 6H), 7.90 (dd, 2H), 8.1 (dd, 2H).

The molecular weight (m+) was 472.

EXAMPLE 7

Into a 1-liter flask equipped with a baffle were added 60 g of 2,2-bis(3-phenyl-4-hydroxyphenyl)propane obtained in Example 1, 1 g of p-tert-butylphenol as the molecular weight regulator, and 500 militarize of methylene chloride. After dissolving the mixture, 300 milliliters of water and 1 milliliter of triethylamine as the catalyst was added and phosgene gas was then blown through the mixture with stirring at temperatures of from 20° to 30° C. at a rate of from 300 to 400 ml/min. All the while phosgene gas was blown through the mixture, a 12N aqueous sodium hydroxide solution was added dropwise to maintain the pH of the reaction system above 10. After phosgene gas was passed for 25 minutes, the mixture was reacted with stirring for 1 hour at temperatures of from 20° to 25° C. After the conclusion of the reaction, the product was diluted with 700 milliliters of methylene chloride, washed with successive, water, a 0.01N aqueous sodium hydroxide solution, water, 0.01N hydrochloric acid, and water, and poured into 5 liters of methanol to precipitate a polymer, and the polymer was then recovered. The yield of the polymer was 64 g (yield: 97%).

The obtained polymer had a reduced viscosity [η sp/c] of 0.42 dl/g as measured in methylene chloride at a concentration of 0.5 g/dl at 20° C. The infrared spectrum of the polymer had an absorption band at 165 cm$^{-1}$ caused by carbonyl groups (C=O) and an absorption band at 1240 cm$^{-1}$ caused by carbon-oxygen bonds (C—O) were observed, and thus the polymer was determined to have carbonate bonds and to be a polycarbonate comprising the following repeating units. The refractive index of the polycarbonate at 20° C. was as large as 1.6662.

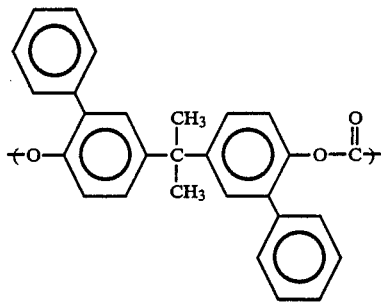

The polymer had a glass transition temperature of 134° C. Then, the polymer was molded into bar-flow moldings by using a Minimat molder produced by Sumitomo Heavy Industries, Ltd. The birefringence of the moldings measured with an elipsometer was on the average 80 nm on the basis of the optical path difference, and the value shows that the polymer has excellent optical property.

EXAMPLE 8

The procedure of Example 7 was repeated with the exception that 65 g of 1-phenyl-1,1-bis(3-phenyl-4-hydroxyphenyl)ethane obtained in Example 2, to obtain a polymer. The resulting polymer had a reduced viscosity [η sp/c] of 0.45 dl/g and a refractive index of 1.6750. By the results of infrared absorption spectrum analysis, the polymer was determined to have carbonate bonds and the following repeating units. The polymer had a glass transition temperature of 174° C. and a birefringence of 37 nm.

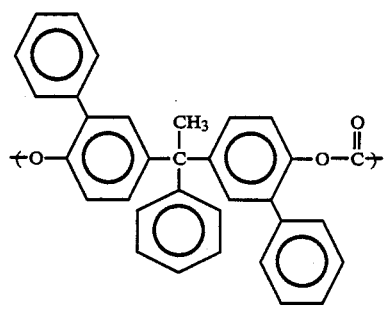

EXAMPLE 9

The procedure of Example 7 was repeated with the exception that 1,1-bis(3-phenyl-4-hydroxyphenyl)cyclohexane obtained in Example 3 was used as the dihydric phenol to obtain a polymer having a reduced viscosity of 0.59 dl/g. By the results of infrared absorption spectrum analysis of the polymer, which showed the same absorptions as those in Example 7, the polymer was determined to be a polycarbonate having the following repeating units. The polymer had a glass transition temperature of 161° C. and a birefringence measured in the form of a molding of 75 nm.

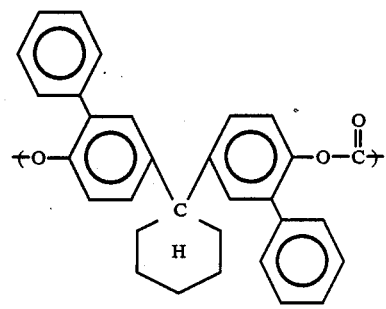

EXAMPLE 10

The procedure of Example 7 was repeated with the exception that 67.6 g (0.2 mol) of 3,3'-diphenyl-4,4'-dihydroxybiphenyl was used as the dihydric phenol to obtain a polymer having a reduced viscosity [η sp/c] of 0.54 dl/g. By the results of infrared absorption analysis of the polymer, which showed the same absorptions as those of Example 7, the polymer was determined to be a polycarbonate having the following repeating units. The polymer had a glass transition temperature of 138° C. and a birefringence of 65 nm.

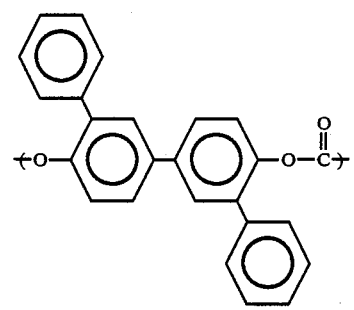

EXAMPLE 11

As the dihydric phenol, 60.3 g (0.15 mol) of bis(3-phenyl-4-hydroxyphenyl)sulfone obtained in Example was dissolved in 500 milliliters of a 2N aqueous sodium hydroxide solution. To the solution were added 400 milliliters of methylene chloride, 1 milliliter of triethylamine as the catalyst, and 0.5 g of p-tert-butylphenol. Thereafter, phosgene gas was blown through the mixture with stirring vigorously in a rate of 300 ml/min. for 15 minutes, and reaction was then carried out with stirring for one hour. The reaction product was then diluted with 1 liter of methylene chloride and washed with successive, 0.01N hydrochloric acid and water.

The product was then poured into methanol to precipitate and recover a polymer. The reduced viscosity [η sp/c] of the polymer was 0.48 dl/g. By the results of infrared absorption analysis of the polymer, which showed the same absorptions caused by polycarbonate bonds as those in Example 5, the polymer was determined to be a polycarbonate having the following repeating units. The polymer had a glass transition temperature of 172° C. and a birefringence of 58 nm.

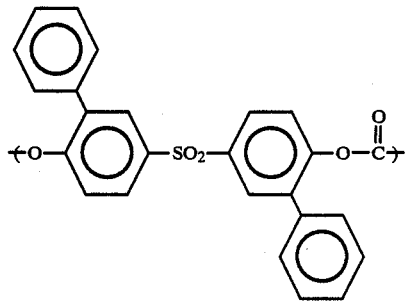

EXAMPLE 12

As the dihydric phenol, 80 g of 1-(4-phenoxyphenyl)-1,1-bis(3-phenyl-4-hydroxyphenyl)ethane obtained in Example 5 was dissolved in 500 milliliters of a 1.5N aqueous potassium hydroxide solution. To the solution were added 400 milliliters of methylene chloride, 1.0 g of p-tert-butylphenol, and 2 milliliters of a 10% by weight aqueous triethylamine solution, and reaction was carried out with vigorously stirring while phosgene gas was passed in for 20 minutes.

After the conclusion of the reaction, the product was diluted with 1 liter of methylene chloride, and washed with successive, 500 milliliters of a 0.01N aqueous sodium hydroxide solution, 500 milliliters of water, 500 milliliters of 0.01N hydrochloric acid, and 500 ml of water. The methylene chloride solution was then subsequently poured into methanol to obtain a white polymer. The reduced viscosity [η sp/c] of the polymer was 0.54 dl/g. The glass transition temperature of the polymer was 160° C. The infrared spectrum of the polymer had an absorption band at 1750 cm$^{-1}$ caused by carbonyl groups (C=O) and an absorption band at 1250 cm$^{-1}$ caused by carbon-oxygen bonds (C—O). The results of $^1$H-NMR (CDCl$_3$) were as follows:

δ (ppm): 2.1 (s, 3H), 6.8–8.0 (m, 25H).

By these results, the polymer was determined to be a polycarbonate comprising the following repeating units.

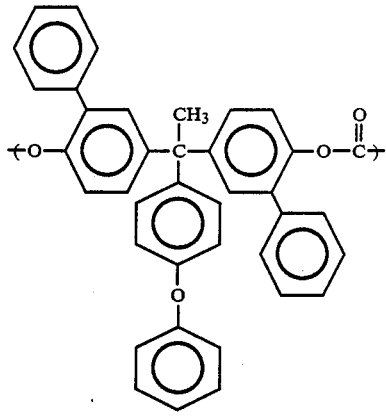

The birefringence of the polymer was 70 nm.

EXAMPLE 13

The procedure of Example 12 was repeated with the exception that 1-(4-methoxyphenyl)-1,1-bis(3-phenyl-4-hydroxyphenyl)ethane obtained in Example 6 was used as the dihydric phenol. The resulting polymer had an reduced viscosity [η sp/c] of 0.52 dl/g and a glass transition temperature of 164° C. The results of $^1$H-NMR (CDCl$_3$) were as follows.

δ (ppm): 2.2 (s, 3H), 3.8 (s, 3H), 6.9–8.0 (m, 20H).

By these results, the polymer was determined to be a polycarbonate having the following repeating units. The birefringence of the polymer was 42 nm.

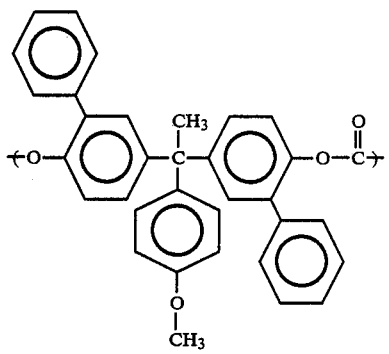

EXAMPLE 14

Into a 1-liter flask equipped with a baffle were placed a solution of 70 g (0.25 mol) of 2,2-bis(4-hydroxyphenyl)propane dissolved in 480 milliliters of a 6% by weight aqueous sodium hydroxide solution and 250 milliliters of methylene chloride, and phosgene gas was blown into the flask with stirring for 14 minutes in a rate of 900 ml/min. Then, the product was subsequently separated by allowing to stand and a methylene chloride solution of a polycarbonate oligomer of a polymerization degree of from 2 to 3 that had chloroformate end groups was obtained.

Subsequently, 90 milliliters of the solution was diluted to 120 milliliters with methylene chloride, and 0.8 g of p-tert-butylphenol as the molecular weight regulator and 14.5 g of 2,2-bis(3-phenyl-4-hydroxyphenyl)propane were then added. 1 milliliter of a 5% by weight aqueous triethylamine solution as the catalyst and 40 milliliters of water were then added, and 90 milliliters of a 2N aqueous sodium hydroxide solution was added dropwise with stirring over a 30-minutes period, and the reaction was carried out with stirring for one hour. After the conclusion of the reaction, the product was diluted by adding 500 milliliters of methylene chloride, and washed with successive, water, a 0.01N aqueous sodium hydroxide solution, 0.01N hydrochloric acid, and water, and then poured into 5 liters of methanol. Thus, 28 g of a copolymer was obtained (yield: 86%).

The copolymer had a reduced viscosity [η sp/c] of 0.48 dl/g as measured in methylene chloride at a concentration of 0.5 g/dl at 20° C. The infrared spectrum had an absorption band at 1650 cm$^{-1}$ caused by carbonyl groups (C=O) and an absorption band at 1240 cm$^{-1}$ caused by carbon-oxygen (C—O), and the copolymer was determined to have carbonate bonds. Further, by the results of NMR spectrum analysis, the mole fraction of the repeating units represented by formula [I] hereinabove was determined to be 33 mol %. By these results, the copolymer was determined to have the following repeating units:

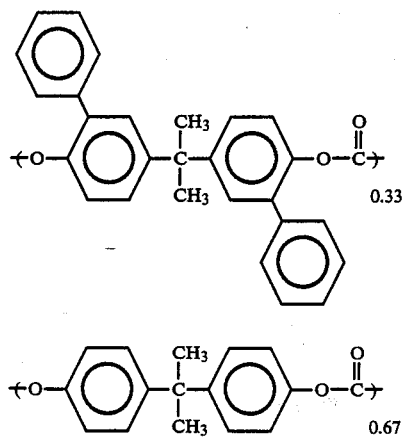

The refractive index at 20° C. of the polycarbonate was 1.6350.

EXAMPLE 15

The procedure of Example 14 was repeated with the exception that the quantity of 2,2-bis(3-phenyl-4-hydroxyphenyl)propane was changed to 7.2 g to obtain a polycarbonate copolymer having a reduced viscosity [η sp/c] of 0.43 dl/g. The copolymer had the following repeating units and a refractive index of 1.610.

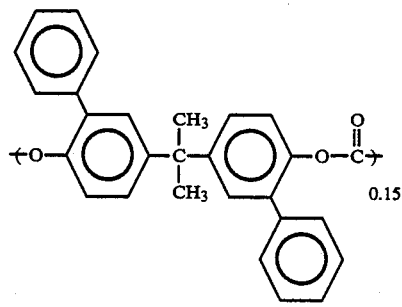

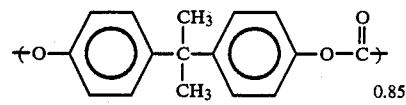

EXAMPLE 16

45 milliliters of a methylene chloride solution of the polycarbonate oligomer obtained in Example 14 was diluted to 60 milliliters with methylene chloride, and 0.4 g of p-tert-butylphenol was added thereto with stirring. Then, 4.9 g of 1-phenyl-1,1-bis(3-phenyl-4-hydroxyphenyl)ethane was dissolved in a mixed solution of 10 milliliters of pyridine and 10 milliliters of methylene chloride, and added dropwise with stirring. The reaction was then carried out with stirring for one hour at room temperature. After the conclusion of the reaction, the product was diluted with 300 milliliters of methylene chloride, and washed with successive, 2N hydrochloric acid and water. The product was then subsequently poured into 2 liters of methanol to precipitate and recover a copolymer.

The resulting copolymer had a reduced viscosity [η sp/c] of 0.38 dl/g. By the results of infrared absorption spectrum analysis and NMR spectrum analysis, the copolymer was determined to have the following repeating units.

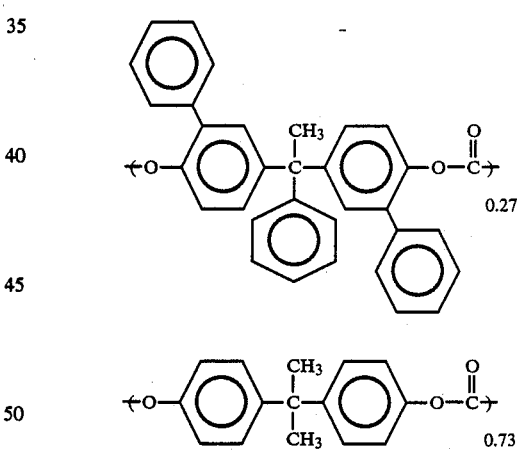

The refractive index of the copolymer was 1.6558 at 20° C.

COMPARATIVE EXAMPLE 1

The refractive index of a polycarbonate (reduced viscosity: 0.51 dl/g), that is prepared by conventional phosgene process by the use of 2,2-bis(4-hydroxyphenyl)propane as the dihydric phenol was 1.5850, at 20° C. The glass transition temperature was 148° C., and the birefringence was as large as 240 nm.

What is claimed is:

1. A polycarbonate polymer exhibiting improved optical properties consisting essentially of repeating units represented by the following general formula:

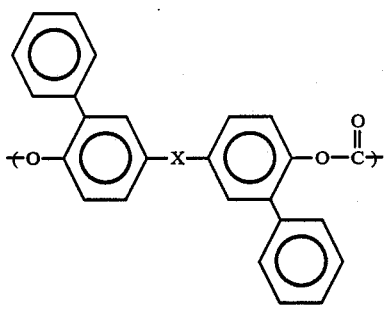

wherein: X is selected from

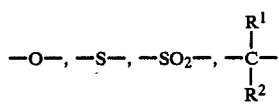

wherein: $R^1$ is selected from hydrogen atom; alkyl radicals of 1 to 6 carbon atoms; cycloalkyl radicals of 5 to 6 carbon atoms;

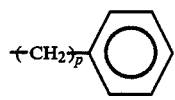

wherein p is an integer having a value of from 0 to 3; phenyl radicals substituted at para position by a substituent selected from alkoxy radicals of 1 to 5 carbon atoms, phenoxy radical, or halogen radicals; or p-biphenylyl radical, and $R^2$ is selected from hydrogen atom; cycloalkyl radicals of 5 to 6 carbon atoms;

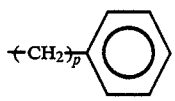

wherein p is an integer having a value of from 0 to 3; phenyl radicals substituted at para position by a substituent selected from alkoxy radicals of 1 to 5 carbon atoms, phenoxy radical, or halogen radicals; or p-biphenylyl radical, $-(CH_2)_q-$ wherein q is an integer having a value of from 2 to 10, or

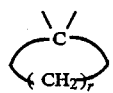

wherein r is an integer having a value of from 4 to 8, and having a reduced viscosity [η sp/c] of at least 0.2 dl/g as measured in methylene chloride at a concentration of 0.5 g/dl at 20° C.

2. A polycarbonate polymer as defined in claim 1 wherein X represents

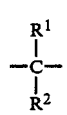

wherein $R^1$ and $R^2$ are as defined above.

3. A polycarbonate polymer as defined in claim 2 wherein $R^1$ is selected from alkyl radicals of 1 to 6 carbon atoms, and $R^2$ is selected from

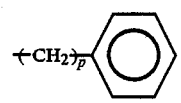

wherein p is an integer having a value of from 0 to 3; or phenyl radicals substituted at para position by a substituent selected from alkoxy radicals of 1 to 5 carbon atoms, phenoxy radical, or halogen radicals.

4. A polycarbonate polymer as defined in claim 3 wherein X is

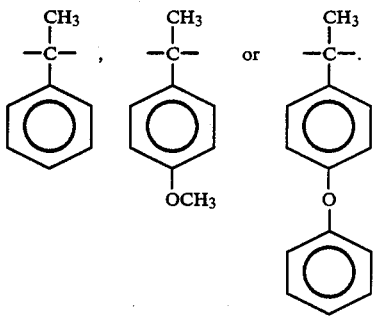

5. A polycarbonate polymer as defined in claim 1, wherein X is

wherein r is an integer having a value of from 4 to 8.

6. A polycarbonate polymer as defined in claim 5, wherein X is

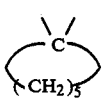

7. A polycarbonate polymer as defined in claim 1, wherein X is $-SO_2-$.

8. A polycarbonate copolymer exhibiting improved optical properties consisting essentially of repeating units represented by the following general formula:

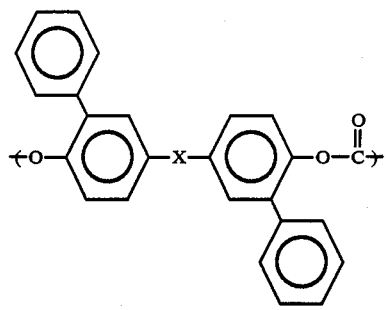

and repeating units represented by the following general formula:

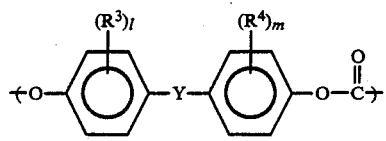

wherein: X and Y are each independently selected from

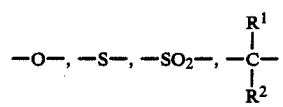

wherein: $R^1$ in X in formula [I] is selected from hydrogen atom; alkyl radicals of 1 to 6 carbon atoms; cycloalkyl radicals of 5 to 6 carbon atoms;

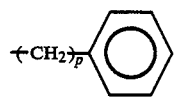

wherein p is an integer having a value of from 0 to 3; phenyl radicals substituted at para position by a substituent selected from alkoxy radicals of 1 to 5 carbon atoms, phenoxy radical, or halogen radicals; or p-biphenylyl radical, $R^2$ in X in formula [I] is selected from hydrogen atom; cycloalkyl radicals of 5 to 6 carbon atoms;

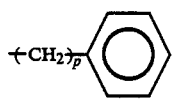

wherein p is an integer having a value of from 0 to 3; phenyl radicals substituted at para position by a substituent selected from alkoxy radicals of 1 to 5 carbon atoms, phenoxy radical, or halogen radicals; or p-biphenylyl radical, and $R^1$ and $R^2$ in Y in formula [III] are each independently selected from hydrogen atom; alkyl radicals of 1 to 6 carbon atoms; cycloalkyl radicals of 5 to 6 carbon atoms;

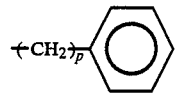

wherein p is an integer having a value of from 0 to 3; phenyl radicals substituted at para position by a substituent selected from alkoxy radicals of 1 to 5 carbon atoms, phenoxy radical, or halogen radicals; or p-biphenylyl radical,

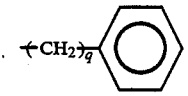

wherein q is an integer having a value of from 2 to 10, or

wherein r is an integer having a value of from 4 to 8, and X and Y are the same or different from each other, $R^3$ and $R^4$ are each independently selected from hydrogen atom, halogen radicals, or alkyl radicals of 1 to 5 carbon atoms, and l and m are independently an integer having a value of from 1 to 4, and having a reduced viscosity [$\eta$ sp/c] of at least 0.2 dl/g as measured in methylene chloride at a concentration of 0.5 g/dl at 20° C.

9. A polycarbonate copolymer as defined in claim 8 wherein X and Y are independently

wherein $R^1$ and $R^2$ are as defined above.

10. A polycarbonate copolymer as defined in claim 9, wherein $R^1$ in X in formula [I] is selected from alkyl radicals of 1 to 6 carbon atoms, and $R^2$ in X in formula [I] is selected from

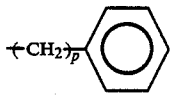

wherein p is an integer having a value of from 0 to 3; or phenyl radicals substituted at para position by a substituent selected from alkoxy radicals of 1 to 5 carbon atoms, phenoxy radical, or halogen radicals.

11. A polycarbonate copolymer as defined in claim 10, wherein X in formula [I] is

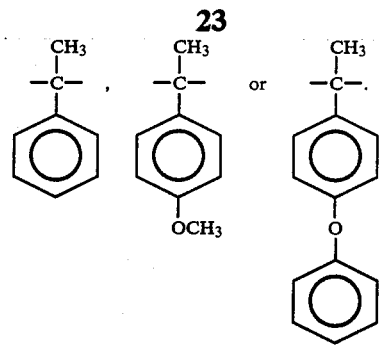
12. A polycarbonate copolymer as defined in claim 9 wherein Y in formula [III] is
* * * * *

UNITED STATES PATENT AND TRADEMARK OFFICE
CERTIFICATE OF CORRECTION

PATENT NO. : 4,892,924

DATED : January 9, 1990

INVENTOR(S) : SHIGEMATSU et al.

It is certified that error appears in the above-identified patent and that said Letters Patent is hereby corrected as shown below:

On the Title Page:

The title is incorrect; should read as follows:

--POLYCARBONATE FROM BIS(3-PHENYL-4-HYDROXYPHENYL) CONTAINING COMPOUND--

Signed and Sealed this

Tenth Day of September, 1991

Attest:

HARRY F. MANBECK, JR.

*Attesting Officer*   *Commissioner of Patents and Trademarks*